United States Patent

Ueno et al.

[11] Patent Number: 5,107,014
[45] Date of Patent: Apr. 21, 1992

[54] PROSTAGLANDIN I ANALOGUE

[75] Inventors: Ryuzo Ueno; Ryuji Ueno, both of Nishinomiya; Tomio Oda, Sanda, all of Japan

[73] Assignee: K.K. Ueno Seiyaku Oyo Kenkyujo, Osaka, Japan

[21] Appl. No.: 521,621

[22] Filed: May 10, 1990

[51] Int. Cl.$^5$ ............ C07C 59/46; C07C 177/00
[52] U.S. Cl. ............ 560/121; 560/53; 562/462; 562/501
[58] Field of Search ............ 560/119, 53; 562/501, 562/402

[56] References Cited

U.S. PATENT DOCUMENTS 4,479,966  10/1984  Hayashi ............ 514/530

FOREIGN PATENT DOCUMENTS 60-69054   4/1985  Japan ............ 514/530
02131446   5/1990  Japan ............ 560/119

Primary Examiner—Robert Gerstl
Attorney, Agent, or Firm—Sughrue, Mion, Zinn, Macpeak & Seas

[57] ABSTRACT

The present invention relates to a new prostagrandine I analogous compounds represented by the following formula (I) and (II).

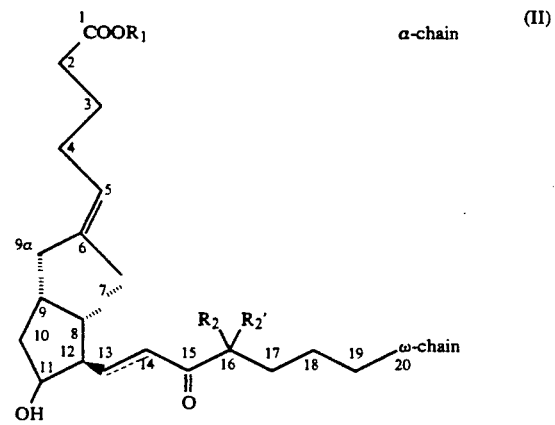

wherein $R_1$ is a hydrogen atom or alkyl group, at least one of $R_2$ and/or $R_2'$ are a halogen atom, an alkyl group, a group containing an aromatic group, a hydroxyl group or an alkoxy group providing that the $R_2$ and $R_2'$ are not simultaneously hydrogen atoms or salt thereof, which compound is expected as hypotensives.

5 Claims, No Drawings

5,107,014

PROSTAGLANDIN I ANALOGUE

BACKGROUND OF THE INVENTION

The present invention relates to a novel compound, a prostaglandin I analogue, which is referred to as PGIs simply hereinafter.

It has been well known that $PGI_2$ has a platelet aggregation controlling effect and a hypotensive activity, but it simultaneously has some side effects such as increasing of pulse rate, hot flush, abdominalgia and the like (S. M. M. Karim et al, PG. Med., 9, 307(1982)).

Japanese Patent Application KOKAI No.61-78734 discloses an effectivity of tricarbonyl-aromatic-group VIB metals complex as a catalyst for reduction of $\alpha,\beta$-unsaturated carbonyl compound, and the production of {(1S,2R,3R,5S)-(E)-7-(4-carbomethoxybutylidene)-2-(3-oxooctyl)-3-tetrahydropyranyloxy-bicyclo[3.3.0]octane} by the reaction of {(1S,5S,6S,7R)-3-(4-carbomethoxy-1(EZ)butenyl)-6-(3-oxo-(E)-1-octenyl)-7-tetrahydropyranyloxybicyclo[3.3.0]octane} in the Example 7. Further, Japanese Patent Application KOKAI No. 61-37740 disclose the same compounds as the above in the Example 7. However, any prior arts as referred do not disclose the PGIs (I) and (II) of the present invention, and any usefulness thereof.

SUMMARY OF THE INVENTION

The present invention provides a novel compound of PGIs represented by the following formula (I) and (II):

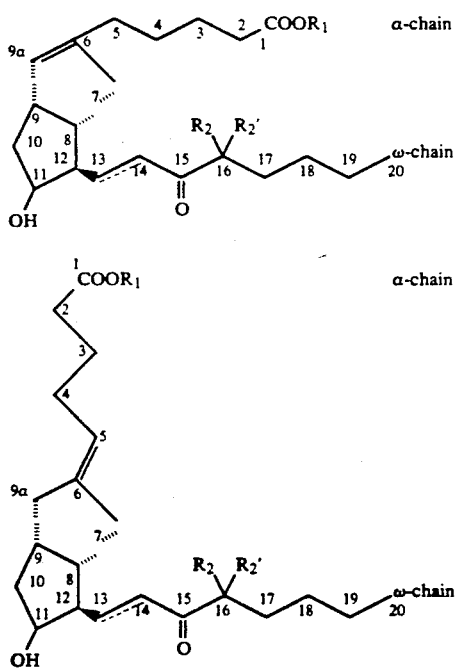

wherein $R_1$ is a hydrogen atom or an alkyl group, and at least one of $R_2$ and/or $R_2'$ are a halogen atom, an alkyl group, a group containing an aromatic group, a hydroxyl group or an alkoxy group or salts thereof.

The PGIs represented by the formula (I) are generally named as 15-keto-16-substituted-9(O)-methano-$\Delta^{6(9\alpha)}$-PGI$_1$s or 13,14-dihydro-15-keto-16-substituted-9(O)-methano-$\Delta^{6(9\alpha)}$-PGI$_1$s; and the PGIs represented by the formula (II) are generally named as 15-keto-16-substituted-9(O)-methano-PGI$_2$ or 13,14-dihydro-15-keto-16-substituted-9(O)-methano-PGI$_2$s.

The PGIs of the present invention is characterized by a bicyclic ring in the molecular skeleton and by one or two specific substituents at the 16-position. Such substituent(s) contributes to a blood pressure hypotension, and reduction of side effects such as increase of pulse rate, and other pharmaceutical or physiological activities of PGIs.

A group represented by the $R_2$ and $R_2'$ includes a halogen atom such as a fluorine atom, a chlorine atom and the like; an alkyl group such as methyl, and ethyl; a group containing an aromatic group such as phenyl, and benzyl; a hydroxyl group; an alkoxy group such as methoxy, and ethoxy. One or both of $R_2$ and/or $R_2'$ being a halogen atom, especially a fluorine atom are most preferable.

$R_1$ in the present invention is a hydrogen atom or alkyl group. As the alkyl group methyl, ethyl, n-propyl, isopropyl, n-butyl, t-butyl group and the like are included. When $R_1$ is a hydrogen atom, corresponding carboxyl group may form a suitable salt. When the compound of the present invention is used for a pharmaceutical composition, the salt may be a physiologically acceptable one. Alkali forming such a salt typically includes an alkaline metal such as sodium, potassium and the like, an alkaline earth metal such as calcium, magnesium and the like, ammonia, alkylamine, alkanolamine such as monoethanolamine, diethanolamine, triethanolamine, propanolamine and the like, alkylalkanolamine and the like.

The 13,14-dihydro-PGI$_1$s represented by (I) and saturated at the $C_{13}$–$C_{14}$ bond can be prepared, for instance, according to the Synthetic Scheme [I]. That is, commercially available (1S,5S,6R,7R)-6-(trialkylsiloxymethyl)-3-formyl-7-tetrahydropyranyloxybicyclo[3.3.-0]octo-2-ene (aldehyde compound (1)) is reacted with ylide which is separately prepared from (3-carboxypropyl)triphenylphosphine bromide and potassium t-butoxide, and then the resultant is reacted with diazomethane to give an ester (2). The ester (2) is subjected with tetra n-butylammonium fluoride to remove the silyl group to yield the alcohol (3). This alcohol (3) is subjected to Collins oxidation to give the aldehyde (4), which is then reacted with an anion prepared from dimethyl(2-oxo-3-substituted-heptyl)phosphonates and sodium hydride so as to introduce $\omega$-chain. The double bond in the $\omega$-chain is hydrogenated with palladium/-carbon and the like under hydrogen atmosphere. In this process a double bond in $\omega$-chain, if there is, is hydrogenated, but a double bond in the ring is not. The tetrahydropyranyl group, a protective group, is removed with an acid to give an ester (7) of an objective compound (I). An acid corresponding to the ester (7) can be obtained by hydrolysis of the ester (7) according to a usual work-up. Though as an example of phosphonates which can be used for introduce of $\omega$-chain one having a fluorine atom at the 3-position as a substituent is illustrated in the Example 1, this substituent may be a halogen such as a chlorine atom; or others such as a methyl, ethyl, phenyl, benzyl, hydroxyl, methoxy or ethoxy group and the like.

PGI$_1$s represented by the formula (I) and having a double bond between $C_{13}$–$C_{14}$ can be prepared according to a process illustrated by the Synthetic Scheme [II]. In this process the ester (2) which can be prepared according to the same manner as in the Scheme [I] is hydrogenated using palladium/carbon under hydrogen atmosphere to give 4-carbomethoxybutyl compounds (2'). This compound (2') is subjected with tetra n-butylammonium fluoride to remove the silyl group to yield the alcohol (3'). This alcohol (3') is subjected to Collins oxidation to give the aldehyde (4'), which is then reacted with an anion which is prepared from dimethyl(2-oxo-3-substituted-heptyl)phosphonates and sodium hydride to introduce ω-chain to give the 15-keto compound (5'). The tetrahydropyranyl group, a protective group, is removed with an acid to give an ester (7') of an objective compound (I). An acid corresponding to the ester (7') can be obtained by hydrolysis of the ester (7') according to a usual work-up. Though as an example of phosphonates which can be used for introduction of ω-chain one having a fluorine atom at the 3-position as a substituent is illustrated in the Example 4, this substituent may be a halogen atom such as a chlorine atom; or other groups such as a methyl, ethyl, phenyl, benzyl, hydroxyl, methoxy or ethoxy group and the like.

16,16-Difluoro compound (9) can be prepared by reacting an anion derived from dimethyl(2-oxo-3,3-difluoroheptyl)phosphonate with the aldehyde (4') as illustrated in the Synthetic Scheme [III].

13,14-Dihydro-PGI₂s represented by the formula (II) can be prepared according to the Synthetic Scheme [IV]. The compound (5) which can be prepared according to the same manner as illustrated in the Scheme [I] can be hydrogenated using tricarbonyl chromium methyl benzoate complex (refer to Japanese Patent Application KOKAI No.61-37740) (in this case the two double bonds on the α-chain and in the ring, which conjugate each other are also hydrogenated to one double bond between the carbon atoms bonding the ring and the α-chain). The obtained compound is treated with an acid to remove the tetrahydropyranyl group to yield an ester (15') of the objective compound (II). Alternatively, the compound (11) obtained in the above process is reduced with sodium borohydride to alcohol, and then the alcohol is hydrolyzed with an alkali to give a carboxylic acid (13). The objective carboxylic acid (15) can be obtained by removing the tetrahydropyranyl group by hydrolysis after Jones oxidation. In the Scheme [IV] a fluorine atom is shown as a substituent on the carbon atom adjacent to the carbonyl group, but another substituent as explained hereinbefore may be used.

PGIs represented by the formula (II) can be prepared from the compound (5) which can be obtained according to the processes illustrated the Synthetic Scheme [V]. The carbonyl group of the compound (5) is reduced using sodium borohydride to give a 15-hydroxy compound (5''), which compound (5'') is then hydrogenated using tricarbonyl chromium benzoic acid methyl complex (see Japanese Patent Application KOKAI No. 61-37740) (in this case two double bonds on the α-chain and in the ring, which conjugates each other are also hydrogenated to one double bond between the carbon atoms bonding the ring and the α-chain).

The obtained compound (12) was hydrolyzed with alkali to an acid (13'), which acid (13') is then oxidized by Jones oxidation to give a ketone (14'). From the ketone (14') is removed the tetrahydropyranyl group by an acid to yield the objective carboxylic acid (15'). The substituent(s) on the carbon atom adjacent to the carbonyl group may be other atom(s) or group(s) as aforementioned.

16,16-Difluoro compound (21) can be prepared by reacting an anion derived from dimethyl(2-oxo-3,3-difluoroheptyl)phosphonate with aldehyde (4) as illustrated in the Synthetic Scheme [VI].

The PGIs of the present invention may include isomers or mixture of isomers. As isomers there are exemplified a keto-hemiacetal tautomers between hydroxyl group at 11-position and carbonyl group at 15-position and optical isomers, geometric isomers and the like.

The present invention is illustrated by Examples, in which compounds are nominated according to IUPAC excepting final objective compounds. The carbon number of the bicyclic ring is indicated as follows:

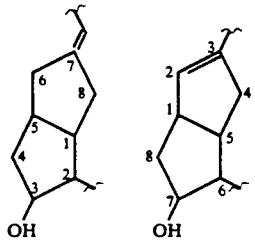

EXAMPLE 1

Preparation of 13,14-dihydro-15-keto-16(RS)-fluoro-9(O)-methano-Δ⁶⁽⁹ᵅ⁾-PGI₁ methyl ester 1-1 Synthesis of (1S,5S,6S,7R)-6-(t-butyldimethylsiloxymethyl)-3-[4-carbomethoxy-1(EZ)-butenyl]-7-tetrahydropyranyloxy-bicyclo[3.3.0]octo-2-ene (2):

Commercially available (1S,5S,6S,7R)-6-(t-butyldimethylsiloxymethyl)-3-formyl-7-tetrahydropyranyloxybicyclo[3.3.0]octo-2-ene (1.00 g) (1) was reacted with ylide which was prepared from (3-carboxypropyl)triphenylphosphine bromide and potassium t-butoxide. A crude carboxylic acid was obtained according to a usual work-up. The product was reacted with diazomethane in ether. A crude product obtained after a usual work-up was purified on a column chromatography (hexane/ethyl acetate=10/1) to give (1S,5S,6S,7R)-6-(t-butyldimethylsiloxymethyl)-3-[4-carbomethoxy-1(EZ)-butenyl]-7-tetrahydropyranyloxybicyclo[3.3.0]octo-2-ene (2) as a colorless oily product. Yield: 0.85 g (67%)

¹H NMR (CDCl₃) δ0.05 (6H,s), 0.90 (9H,s), 1.05–1.95 (10H,m), 2.10–3.13 (7H,m), 3.27–4.22 (5H,m), 3.63 (3H,s), 4.45–4.69 (1H,m), 5.05–5.65(2H,m), 5.97 (0.67H,d, J=12 Hz), 6.22 (0.33H, d, J=16 Hz)

1-2 Synthesis of (1S,5S,6S,7R)-3-[4-carbomethoxy-1(EZ)-butenyl]-6-hydroxymethyl-7-tetrahydropyranyloxybicyclo[3.3.0]octo-2-ene (3):

(1S,5S,6S,7R)-6-(t-Butyldimethylsiloxymethyl)-3-[4-carbomethoxy-1(EZ)-butenyl]-7-tetrahydropyranyloxybicyclo[3.3.0]octo-2-ene (2) obtained in 1-1 (0.85 g) was dissolved in THF, into which tetra-n-butylammonium fluoride in THF (1.1M, 6.43 ml) was added, and the mixture was stirred for 18 hours. A crude product obtained after a usual work-up was purified on column chromatography (hexane/ethyl acetate=1/1) to give (1S,5S,6S,7R)-3-[4-carbomethoxy-1(EZ)-butenyl]-6-hydroxymethyl-7-tetrahydropyranyloxy-bicyclo[3.3.0]octo-2-ene (3) as a colorless oily product. Yield: 0.59 g (96%)

¹H NMR (CDCl₃) δ1.18~1.93(10H,m), 2.16~3.28(8H,m), 3.42~4.07(5H,m), 3.63(3H, s), 4.55~4.64(0.5H,m), 4.66~4.77(0.5H,m), 5.33(0.67H, dt, J=7.5 Hz, J=12.5 Hz), 5.42~5.67(1.33H,m), 5.99(0.67H,d,J=12.5 Hz), 6.26(0.33H,d,J=15.5 Hz).

1-3 Synthesis of (1S,5S,6S,7R)-3-[4-carbomethoxy-1(EZ)-butenyl]-6-[4(RS)-fluoro-3-oxo-(E)-1-octenyl]-7-tetrahydropyranyloxy-bicyclo[3.3.0]octo-2-ene (5):

(1S,5S,6S,7R)-3-[4-Carbomethoxy-1(EZ)-butenyl]-6-hydroxymethyl-7-tetrahydropyranyloxy-bicyclo[3.3.0]octo-2-ene (3) (0.240 g) was subjected to Collins oxidation in methylene chloride at 0° C. Into the reaction mixture was added sodium hydrogen sulfonate, and filtered. A crude aldehyde (4) obtained after concentration under reduced pressure of the filtrate was dissolved in THF, and reacted with an anion which was prepared from dimethyl (2-oxo-3-fluoroheptyl) phosphonate (0.61 g) and sodium hydride as stirring at 50° C. for 5 hours. The reaction mixture was neutralized with acetic acid. A crude product obtained after a usual work-up was purified on column chromatography (hexane/ethyl acetate=6/1) to give (1S,5S,6S,7R)-3-[4-carbomethoxy-1(EZ)-butenyl]-6-[4(RS)-fluoro-3-oxo-(E)-1-octenyl]-7-tetrahydropyranyloxy-bicyclo[3.3.0]octo-2-ene (5) as a pale yellow oily product. Yield: 0.250 g (85%)

¹H NMR(CDCl₃)δ 0.70~1.07(3H,m), 1.06~2.14(15H,m), 2.15~4.16(11H,m), 3.66(3H,s), 4.43~4.72(1.5H,m), 4.96~5.71(2.5H,m), 5.95(0.67H,d,J=11 Hz), 6.24(0.33H,d,J=16 Hz), 6.36~6.73(1H,m), 6.83~7.23(1H,m).

1-4 Synthesis of(1S,5S,6R,7R)-3-(4-carbomethoxybutyl)-6-[4(RS)-fluoro-3-oxo-octyl]-7-tetrahydropyranyloxy-bicyclo[3.3.0]octo-2-ene (6):

(1S,5S,6S,7R)-3-[4-Carbomethoxy-1(EZ)-butenyl]-6-[4(RS)-fluoro-3-oxo-(E)-1-octenyl]-7-tetrahydropyranyloxy-bicyclo[3.3.0]octo-2-ene (5) (0.094 g) was dissolved in ethyl acetate, into which palladium(5 wt %)/carbon (0.0094 g) was added and stirred under hydrogen atmosphere at 15° C. for 2 hours. The reaction mixture was filtered, and the filtrate was evaporated under reduced pressure. Obtained crude product was chromatographed using a silica gel treated with silver nitrate (15 wt %) (hexane/ethyl acetate=12-/1-9/1) to give (1S,5S,6R,7R)-3-(4-carbomethoxybutyl)-6-[4(RS)-fluoro-3-oxo-octyl]-7-tetrahydropyranyloxybicyclo[3.3.0]octo-2-ene (6) as a pale yellow oily product. Yield: 0.042 g (44%)

¹H NMR(CDCl₃)δ 0.66~1.03(3H,m), 1.03~3.12(31H,m), 3.24~4.02(3H,m), 3.63(3H,s), 4.27~4.53(0.5H,m), 4.50~4.70(1H,m), 4.83~5.06(0.5H,m), 5.06~5.33(1H,m).

1-5 Synthesis of 13,14-dihydro-15-keto-16(RS)-fluoro-9(O)-methano-Δ⁶⁽⁹ᵃ⁾-PGI₁ methyl ester:

(1S,5S,6R,7R)-3-(4-Carbomethoxybutyl)-6-[4(RS)-fluoro-3-oxo-octyl]-7-tetrahydropyranyloxybicyclo[3.3.0]octo-2-ene (6) (0.088 g) was dissolved in a mixture of acetic acid, water and THF (4:2:1) and stirred at 45° C. for 4 hours. A reaction mixture was concentrated under reduced pressure, and a crude product obtained was purified on column chromatography (hexane/ethyl acetate=6/1-4/1) to give 13,14-dihydro-15-keto-16(RS)-fluoro-9(O)-methano-Δ⁶⁽⁹ᵃ⁾-PGI₁ methyl ester (7) as a pale yellow product. Yield: 0.072 g (100%)

¹H NMR(CDCl₃)δ 0.73~1.05(3H,m), 1.05~3.15(26H,m), 3.46~4.04(1H,m), 3.63(3H,s), 4.33~4.56(0.5H,m), 4.48~5.07(0.5H,m), 5.07~5.36(1H,m).

EXAMPLE 2

Preparation of 13,14-dihydro-15-keto-16(RS)-fluoro-9(O)-methano-PGI₂

2-1 Synthesis of (1S,2R,3R,5S)-7(E)-(4-carbomethoxybutylidene)-2-[4(RS)-fluoro-3-oxo-octyl]-3-tetrahydropyranyloxy-bicyclo[3.3.0]octane (11):

(1S,5S,6S,7R)-3-[4-Carbomethoxy-1(EZ)-butenyl]-6-[4(RS)-fluoro-3-oxo-(E)-1-octenyl]-7-tetrahydropyranyloxybicyclo[3.3.0]octo-2-ene (5) (0.109 g) was dissolved in acetone in an autoclave, into which a tricarbonyl chromium/methyl benzoate complex (0.023 g) was added. The mixture was degassed and the content was stirred under a hydrogen atmosphere (70 kg/cm²) at 125° C. for 20 hours. The reaction mixture was concentrated under reduced pressure. A crude product obtained was chromatographed (hexane/ethyl acetate=10/1-7/1) to give (1S,2R,3R,5S)-7(E)-(4-carbomethoxybutylidene)-2-[4(RS)-fluoro-3-oxo-octyl]-3-tetrahydropyranyloxy-bicyclo[3.3.0]octane (11) as a colorless oily product. Yield: 0.157 g (99%)

¹H NMR(CDCl₃)δ 0.76~1.05(3H,m), 1.05~2.91(31H,m), 3.27~3.98(3H,m), 3.62(3H,s), 4.31~4.72(1.5H,m), 4.79~5.32(1.5H,m).

2-2 Synthesis of (1S,2R,3R,5S)-7(E)-(4-carbomethoxybutylidene)-2-[4(RS)-fluoro-3(RS)-hydroxy-octyl]-3-tetrahydropyranyloxybicyclo[3.3.0]octane (12):

(1S,2R,3R,5S)-7(E)-(4-Carbomethoxybutylidene)-2-[4(RS)-fluoro-3-oxo-octyl]-3-tetrahydropyranyloxybicyclo[3.3.0]octane (11) (0.197 g) was dissolved in methanol, to which a sodium borohydride (0.017 g) was added at 0° C. The mixture was stirred for 30 minutes and treated as a usual work-up. A crude product obtained was chromatographed (hexane/ethyl acetate=3/1) to give (1S,2R,3R,5S)-7(E)-(4-carbomethoxybutylidene)-2-[4(RS)-fluoro-3(RS)-hydroxy-octyl]-3-tetrahydropyranyloxybicyclo[3.3.0]octane (12). Yield: 0.185 g (93%)

¹H NMR(CDCl₃)δ 0.72~1.05(3H,m), 1.05~2.66(32H,m), 3.22~4.15(4.5H,m), 3.62(3H,s), 4.42~4.67(1.5H,m), 5.00~5.31(1H,m).

2-3 Synthesis of (1S,2R,3R,5S)-7(E)-(4-Carboxybutylidene)-2-[4(RS)-fluoro-3(RS)-hydroxyoctyl]-3-tetrahydropyranyloxybicyclo[3.3.0]octane (13):

(1S,2R,3R,5S)-7(E)-(4-Carbomethoxybutylidene)-2-[4(RS)-fluoro-3(RS)-hydroxy-octyl]-3-tetrahydropyranyloxybicyclo[3.3.0]octane (12) (0.185 g) was dissolved in methanol, to which an aqueous solution of 1N sodium hydroxide (6.5 ml) was added. The mixture was stirred at room temperature for 4 hours. After a usual work-up a crude product (1S,2R,3R,5S)-7(E)-(4-carboxybutylidene)-2-[4(RS)-fluoro-3(RS)-hydroxyoctyl]-3-tetrahydropyranyloxybicyclo[3.3.0]octane (13) was obtained. Yield: 0.184 g 2-4 Synthesis of (1S,2R,3R,5S)-7(E)-(4-carboxybutylidene)-2-[4(RS)-fluoro-3-oxooctyl]-3-tetrahydropyranyloxybicyclo[3.3.0]octane (14):

(1S,2R,3R,5S)-7(E)-(4-Carboxybutylidene)-2-[4(RS)-fluoro-3(RS)-hydroxyoctyl]-3-tetrahydropyranyloxybicyclo[3.3.0]octane (13) (0.184 g) was oxidized with Jones reagent between about −15° and −5° C. After stirring for 40 minutes, isopropyl alcohol (0.43 ml) was added, and treated by a usual work-up. Obtained crude product was purified on column chromatography (hexane/ethyl acetate=15/1-10/1) using silica gel treated with an acid (CC-4: available from Mallineckrodt Co., Ltd.) to give (1S,2R,3R,5S)-7(E)-(4-carboxybutylidene)-2-[4(RS)-fluoro-3-oxooctyl]-3-tetrahydropyranyloxybicyclo[3.3.0]octane (14) as a colorless oily product. Yield: 0.072 g (40%)

$^1$H NMR(CDCl$_3$)δ 0.72~1.04(3H,m), 1.04~2.88(31H,m), 3.20~3.98(3H,m), 4.20~4.68(1.5H,m), 4.75~5.33(1.5H,m), 6.52~8.52(1H,brs).

2-5 Preparation of 13,14-dihydro-15-keto-16(RS)-fluoro-9(O)-methano-PGI$_2$ (15):

(1S,2R,3R,5S)-7(E)-(4-Carboxybutylidene)-2-[4(RS)-fluoro-3-oxooctyl]-3-tetrahydropyranyloxybicyclo[3.3.0]octane (14) (0.070 g) was dissolved in a mixture of acetic acid, water and THF (4:2:1) and stirred at 45° C. for 3.5 hours. The reaction mixture was concentrated under reduced pressure. A crude product obtained was purified on column chromatography (hexane/ethyl acetate=3.5/1) using a silica gel (CC-4) to give 13,14-dihydro-15-keto-16(RS)-fluoro-9(O)-methano-PGI$_2$ (15) as a colorless oily product. Yield: 0.048 g (84%)

$^1$H NMR(CDCl$_3$)δ 0.65~1.05(3H,m), 1.05~2.85(25H,m), 3.43~3.82(1H,m), 4.26~4.57(0.5H,m), 4.76~5.35(1.5H,m), 5.20~6.57(2H,brs).

EXAMPLE 3

Preparation of 13,14-dihydro-15-keto-16(RS)-fluoro-9(O)-methano-PGI$_2$ methyl ester (15')

(1S,2R,3R,5S)-7(E)-(4-Carbomethoxybutylidene)-2-[4(RS)-fluoro-3-oxo-octyl]-3-tetrahydropyranyloxybicyclo[3.3.0]octane (11) (0.070 g) was dissolved in a mixture of acetic acid, water and THF (4:2:1), and stirred at 45° C. for 3 hours. The reaction mixture was concentrated under reduced pressure, and crude product obtained was purified on column chromatography (hexane/ethyl acetate=3.5/1) to give 13,14-dihydro-15-keto-16(RS)-fluoro-9(O)-methano-PGI$_2$ methyl ester (15') as a colorless oily product. Yield: 0.038 g (67%)

$^1$H NMR(CDCl$_3$) δ 0.75~1.05(3H,m), 1.05~2.87(26H,m), 3.37~3.96(1H,m), 3.64(3H,s), 4.28~4.53(0.5H,m), 4.77~5.32(1.5H,m).

EXAMPLE 4

Preparation of 16(RS)-fluoro-15-keto-9(O)-methano-Δ$^{6(9\alpha)}$-PGI$_1$ methyl ester 4-1 Synthesis of (1S,5S,6S,7R)-6-(t-butyldimethylsiloxymethyl)-3-[4-carbomethoxy-1(EZ)-butenyl]-7-tetrahydropyranyloxy-bicyclo[3.3.0]octo-2-ene (2):

According to the same manner as in the Example 1, 1-1 the title compound (2) was prepared.

4-2 Synthesis of (1S,5S,6S,7R)-6-(t-butyldimethylsiloxymethyl)-3-(4-carbomethoxybutyl)-7-tetrahydropyranyloxybicyclo[3.3.0]octo-2-ene (2'):

(1S,5S,6S,7R)-6-(t-Butyldimethylsiloxymethyl)-3-[4-carbomethoxy-1(EZ)-butenyl]-7-tetrahydropyranyloxybicyclo[3.3.0]octo-2-ene (2) (0.214 g) was dissolved in methanol, to which palladium (10%)/carbon (0.050 g) was added, and the mixture was stirred under hydrogen atmosphere at room temperature for 45 minutes. The reaction mixture was filtered and the filtrate was concentrated under reduced pressure. A crude product was chromatographed (hexane/ethyl acetate=40/1-30/1) using silica gel treated with silver nitrate (10 wt. %) to give (1S,5S,6S,7R)-6-(t-butyldimethylsiloxymethyl)-3-(4-carbomethoxybutyl)-7-tetrahydropyranyloxybicyclo[3.3.0]octo-2-ene (2') as a colorless oily product. Yield: 0.151 g (70%)

$^1$H NMR(CDCl$_3$)δ 0.05(6H,s), 0.88(9H,s), 0.97~3.03(21H,m), 3.23~4.15(5H,m), 3.62(3H,s), 4.45~4.69(1H,m), 5.10~5.33(1H,m).

4-3 Synthesis of (1S,5S,6S,7R)-3-(4-carbomethoxybutyl)-6-hydroxymethyl-7-tetrahydropyranyloxybicyclo[3.3.0]octo-2-ene (3'):

(1S,5S,6S,7R)-6-(t-Butyldimethylsiloxymethyl)-3-(4carbomethoxybutyl)-7-tetrahydropyranyloxybicyclo[3.3.0]octo-2-ene (2') (0.294 g) was dissolved in THF, into which tetra-n-butyl-ammonium fluoride solution in THF (1.1M, 2.2 ml) was added, and stirred at room temperature for 18 hours. A crude compound obtained after a usual work-up was purified on column chromatography (hexane/ethyl acetate=1/1) to give (1S,5S,6S,7R)-3-(4-carbomethoxybutyl)-6-hydroxymethyl-7-tetrahydropyranyloxybicyclo[3.3.0]octo-2-ene (3') as a colorless oily product. Yield: 0.228 g $^1$H NMR(CDCl$_3$)δ 0.76~3.13(22H,m), 3.27~4.13(5H,m), 3.63(3H,s), 4.46~4.77(1H,m); 5.02~5.42(1H,m).

4-4 Synthesis of (1S,5S,6S,7R)-3-(4-carbomethoxybutyl)-6-[4(RS)-fluoro-3-oxo-(E)-1-octenyl]-7-tetrahydoropyranyloxybicyclo[3.3.0]octo-2-ene (5'):

(1S,5S,6S,7R)-3-(4-Carbomethoxybutyl)-6-hydroxymethyl-7-tetrahydropyranyloxybicyclo[3.3.0]octo-2-ene (3') ((0.125 g) was dissolved in DMSO, to which a solution of triethylamine (0.93 ml) and sulfur trioxide/pyridine complex (0.504 g) in DMSO was added, and stirred at room temperature for 1.5 hours. A crude aldehyde (4') obtained after usual work-up was dissolved in THF, and reacted at 50° C. with the anion prepared from dimethyl(2-oxo-3-fluoroheptyl)phosphonate (0.341 g) and sodium hydride. After stirred for 3 hours, the reaction mixture was neutralized with acetic acid. A crude product obtained according to a usual work-up was purified on column chromatography (hexane/ethyl acetate=7/1) to give (1S,5S,6S,7R)-3-(4-carbomethoxybutyl)-6-[4(RS)-fluoro-3-oxo-(E)-1-octenyl]-7-tetrahydoropyranyloxybicyclo[3.3.0]octo-2-ene (5'). Yield: 0.088 g (56%)

$^1$H NMR(CDCl$_3$)δ 0.75~1.06(3H,m), 1.05~3.14(27H,m), 3.26~4.13(3H,m), 3.63(3H,s), 4.38~4.71(1.5H,m), 5.01~5.43(1.5H,m) 6.26~6.68(1H,m), 6.80~7.26(1H,m).

4-5 Synthesis of 16(RS)-fluoro-15-keto-9(O)-methano-Δ$^{6(9\alpha)}$-PGI$_1$ methyl ester (7'):

(1S,5S,6S,7R)-3-(4-Carbomethoxybutyl)-6-[4(RS)-fluoro-3-oxo-(E)-1-octenyl]-7-tetrahydoropyranyloxybicyclo[3.3.0]octo-2-ene (5') (0.088 g) was dissolved in a mixture of acetic acid, water and THF (4:2:1), and stirred at 45° C. for 3 hours. The reaction mixture was concentrated under reduced pressure, and a crude product obtained was purified on column chromatography (hexane/ethyl acetate=3/1) to give 16(RS)-fluoro-15-keto-9(O)-methano-Δ$^{6(9\alpha)}$-PGI$_1$ methyl ester (7'). Yield: 0.069 g (96%)

$^1$H NMR(CDCl$_3$)δ 0.72~1.04(3H,m), 1.04~3.18(22H,m), 3.62(3H,s), 3.70~4.12(1H,m) 4.43~4.63(0.5H,m), 4.98~5.23(0.5H,m), 5.18~5.35(1H,m), 6.53(1H,dd,J=16 Hz,J=3 Hz), 6.98(1H,dd,J=16 Hz,J=9 Hz).

EXAMPLE 5

Preparation of 16,16-difluoro-15-keto-9(O)-methano-$\Delta^{6(9\alpha)}$-PGI$_1$ methyl ester 5-1 Synthesis of (1S,5S,6S,7R)-3-(4-carbomethoxybutyl)-6-[4,4-difluoro-3-oxo-(E)-1-octenyl]-7-tetrahydropyranyloxybicyclo[3.3.0]octo-2-ene (8):

(1S,5S,6S,7R)-3-(4-Carbomethoxybutyl)-6-hydroxymethyl-7-tetrahydropyranyloxybicyclo[3.3.0]octo-2-ene (3') (0.108 g) was dissolved in DMSO, to which a solution of triethylamine (0.90 ml) and sulfur trioxide/pyridine complex (0.488 g) in DMSO was added, and stirred at room temperature for 30 minutes. A usual work-up gave a crude aldehyde. The crude aldehyde was dissolved in THF, and reacted with an anion prepared from dimethyl(2-oxo-3,3-difluoroheptyl)phosphate (0.435 g) and sodium hydride. The mixture was heated for 48 hours under reflux, and then neutralized with acetic acid. A crude product obtained after a usual work-up was purified on column chromatography (hexane/ethyl acetate=7/1) to give (1S,5S,6S,7R)-3-(4-carbomethoxybutyl)-6-[4,4-difluoro-3-oxo-(E)-1-octenyl]-7-tetrahydropyranyloxybicyclo[3.3.0]octo-2-ene (8) as a colorless oily product. Yield: 0.091 g (64%)

$^1$H NMR(CDCl$_3$)$\delta$ 0.76~1.05(3H,m), 1.05~3.17(27H,m), 3.25~4.15(3H,m), 3.63(3H,s), 4.35~4.75(1H,m), 5.09~5.37(1H,m), 6.56(1H,dd,J=15 Hz,J=6 Hz), 6.86~7.37(1H,m).

5-2 Synthesis of 16,16-difluoro-15-keto-9(O)-methano-$\Delta^{6(9\alpha)}$-PGI$_1$ methyl ester (9):

(1S,5S,6S,7R)-3-(4-Carbomethoxybutyl)-6-[4,4-difluoro-3-oxo-(E)-1-octenyl]-7-tetrahydropyranyloxybicyclo[3.3.0]octo-2-ene (8) (0.091 g) was dissolved in a mixture of acetic acid, water and THF (4:2:1), and stirred at 45° C. for 3 hours. The reaction mixture was concentrated under reduced pressure, and a crude product was purified on column chromatography (hexane/ethyl acetate=2/1) to give 16,16-difluoro-15-keto-9(O)-methano-$\Delta^{6(9\alpha)}$-PGI$_1$ methyl ester (9) as a colorless oily product. Yield: 0.060 g (80%)

$^1$H NMR(CDCl$_3$)$\delta$ 0.76~1.05(3H,m), 1.05~3.21(22H,m), 3.62(3H,s), 3.73~4.17(1H,m), 5.09~5.43(1H,m), 6.56(1H,d,J=15 Hz), 7.12(1H,dd,J=15 Hz,J=7.5 Hz).

EXAMPLE 6

Preparation of 16(RS)-fluoro-15-keto-9(O)-methano-PGI$_2$ 6-1 Synthesis of (1S,5S,6S,7R)-3-[4-carbomethoxy-1(EZ)-butenyl]-6-hydroxymethyl-7-tetrahydropyranyloxybicyclo[3.3.0]octo-2-ene (3):

According to the same manner as in 1-2 of the Example 1 the Compound (3) was prepared.

6-2 Synthesis of (1S,5S,6S,7R)-3-[4-carbomethoxy-1(EZ)-butenyl]-6-[4(RS)-fluoro-3-oxo-(E)-1-octenyl]-7-tetrahydropyranyloxy-bicyclo[3.3.0]octo-2-ene (5):

According to the same manner as in 1-3 of the Example 1 the above Compound (5) was prepared.

6-3 Synthesis of (1S,5S,6S,7R)-3-[4-carbomethoxy-1(EZ)-butenyl]-6-[4(RS)-fluoro-3(RS)-hydroxy-(E)-1-octenyl]-7-tetrahydropyranyloxybicyclo[3.3.0]octo-2-ene (5''):

(1S,5S,6S,7R)-3-[4-Carbomethoxy-1(EZ)-butenyl]-6-[4(RS)-fluoro-3-oxo-(E)-1-octenyl]-7-tetrahydropyranyloxybicyclo[3.3.0]octo-2-ene (5) (0.088g) was dissolved in methanol, into which sodium borohydride (0.008 g) was added at 0° C. and stirred for 30 minutes. The reaction mixture was treated by a usual manner to give (1S,5S,6S,7R)-3-[4-carbomethoxy-1(EZ)-butenyl]-6-[4(RS)-fluoro-3(RS)-hydroxy-(E)-1-octenyl]-7-tetrahydropyranyloxybicyclo[3.3.0]octo-2-ene (5'') as a colorless oily product. Yield: 0.089 g $^1$H NMR(CDCl$_3$)$\delta$ 0.67~1.03(3H,m), 1.03~3.19(24H,m), 3.22~4.34(4.5H,m), 3.62(3H,s), 4.40~4.74(1.5H,m), 5.07~6.32(5H,m).

6-4 Synthesis of (1S,2S,3R,5S)-(E)-7-(4-carbomethoxybutylidene)-2-[4(RS)-fluoro-3(RS)-hydroxy(E)-1-octenyl]-3-tetrahydropyranyloxybicyclo[3.3.0]octane (12'):

(1S,5S,6S,7R)-3-[4-Carbomethoxy-1(EZ)-butenyl]-6-[4(RS)-fluoro-3(RS)-hydroxy-(E)-1-octenyl]-7-tetrahydropyranyloxybicyclo[3.3.0]octo-2-ene (5'') (0.089 g) was put in an autoclave and dissolved in acetone, into which tricarbonyl chromium/methyl benzoate complex (0.011 g) was added, and then degassed. The mixture in the autoclave was stirred under hydrogen pressure of 70 kg/cm$^2$ at 120° C. for 15 hours. The reaction mixture was concentrated under reduced pressure, and the obtained crude product was purified on column chromatography (hexane/ethyl acetate=2/1) to give (1S,2S,3R,5S)-(E)-7-(4-carbomethoxybutylidene)-2-[4(RS)-fluoro-3(RS)-hydroxy(E)-1-octenyl]-3-tetrahydropyranyloxybicyclo[3.3.0]octane (12') as a colorless oily product. Yield: 0.078 g (87%)

$^1$H NMR(CDCl$_3$)$\delta$ 0.70~1.04(3H,m), 1.04~2.67(28H,m), 3.21~4.32(4.5H,m), 4.36~4.75(1.5H,m), 4.99~5.30(1H,m), 5.30~5.92(2H,m).

6-5 Synthesis of (1S,2S,3R,5S)-(E)-7-(4-Carboxybutylidene)-2-[4(RS)-fluoro-3(RS)-hydroxy-(E)-1-octenyl]-3-tetrahydropyrayloxybicyclo[3.3.0]octane (13'):

(1S,2S,3R,5S)-(E)-7-(4-Carbomethoxybutylidene)-2-[4(RS)-fluoro-3(RS)-hydroxy(E)-1-octenyl]-3-tetrahydropyranyloxybicyclo[3.3.0]octane (12') (0.129 g) was dissolved in methanol, into which 1N aqueous solution of sodium hydroxide (2 ml) was added, and stirred at room temperature for 6 hours. After a usual work-up (1S,2S,3R,5S)-(E)-7-(4-carboxybutylidene)-2-[4(RS)-fluoro-3(RS)-hydroxy-(E)-1-octenyl]-3-tetrahydropyranyloxybicyclo[3.3.0]octane (13') was obtained as a colorless oily product. Yield: 0.140 g $^1$H NMR(CDCl$_3$)$\delta$ 0.70~1.05(3H,m), 1.05~2.70(27H,m), 3.26~6.06(10H,m).

6-6 Synthesis of (1S,2S,3R,5S)-(E)-7-(4-carboxybutylidene)-2-[4(RS)-fluoro-3-oxo-(E)-1-octenyl]-3-tetrahydropyranyloxybicyclo[3.3.0]octane (14'):

(1S,2S,3R,5S)-(E)-7-(4-Carboxybutylidene)-2-[4(RS)-fluoro-3(RS)-hydroxy-(E)-1-octenyl]-3-tetrahydropyranyloxybicyclo[3.3.0]octane (13') (0.140 g) was subjected to Jones oxidation between −15° C. and −20° C. The mixture was stirred for 30 minutes, isopropyl alcohol was added, and the resultant was treated by a usual work-up. The obtained crude product was purified on column chromatography (hexane/ethyl acetate=6/1-5/1) to give (1S,2S,3R,5S)-(E)-7-(4-carboxybutylidene)-2-[4(RS)-fluoro-3-oxo-(E)-1-octenyl]-3-tetrahydropyranyloxybicyclo[3.3.0]octane (14') as a colorless oily product. Yield: 0.106 g (76%)

$^1$H NMR(CDCl$_3$)$\delta$ 0.75~1.04(3H,m), 1.04~2.78(27H,m), 3.23~4.14(3H,m), 4.37~4.73(1.5H,m), 5.02~5.36(1.5H,m), 6.32~6.67(1H,m), 6.73~7.26(1H,m).

6-7 Synthesis of 16(RS)-fluoro-15-keto-9(O)-methano-PGI$_2$ (15'):

(1S,2S,3R,5S)-(E)-7-(4-Carboxybutylidene)-2-[4(RS)-fluoro-3-oxo-(E)-1-octenyl]-3-tetrahydropyranyloxybicyclo[3.3.0]octane (14') (0.106 g) was dissolved in a mixture of acetic acid, water and THF (4:2:1), and stirred at 45° C. for 3.5 hours. The reaction mixture was concentrated under reduced pressure. The crude product was purified on column chromatography (hexane/ethyl acetate=6/1–2/1) using silica gel (CC-4: available from Mallineckrodt Co., Ltd.) to give 16(RS)-fluoro-15-keto-9(O)-methano-PGI$_2$ (15') as a colorless oily product. Yield: 0.047 g (52%)

$^1$H NMR(CDCl$_3$)δ 0.74~1.04(3H,m), 1.04~2.80(21H,m), 3.67~4.07(1H,m), 4.43~4.65(0.5H,m), 4.99~5.37(1.5H,m), 4.00~5.60(2H,brs), 6.51(1H,dd,J=17 Hz, J=4 Hz), 6.94(1H,dd,J=17 Hz,J=7 Hz).

EXAMPLE 7

Preparation of 16,16-difluoro-15-keto-9(O)-methano-PGI$_2$ 7-1 Synthesis of (1S,5S,6S,7R)-3-[4-carbomethoxy-1(EZ)-butenyl]-6-[4,4-difluoro-3-oxo-(E)-1-octenyl]-7-tetrahydropyranyloxybicyclo[3.3.0]octo-2-ene (16):

(1S,5S,6R,7R)-3-[4-carbomethoxy-1(EZ)-butenyl]-6-hydroxymethyl-7-tetrahydropyranyloxy-bicyclo[3.3.0]octo-2-ene(3) (0.333 g) was subjected to Collins oxidation in methylene chloride at 0° C. After 30 minutes sodium hydrogen sulfate was added into the reaction mixture, and filtrated. The filtrate was concentrated under reduced pressure to give crude aldehyde (4), which was dissolved in THF, and reacted at 70° C. with an anion prepared from dimethyl(2-oxo-3,3-difluoroheptyl)phosphonate (0.970 g) and sodium hydride. After stirred for 17 hours, the reaction product was neutralized by acetic acid. A crude product obtained after a usual work-up was purified by column chromatography (hexane/ethyl acetate=6/1) to give (1S,5S,6S,7R)-3-[4-carbomethoxy-1(EZ)-butenyl]-6-[4,4-difluoro-3-oxo-(E)-1-octenyl]-7-tetrahydropyranyloxybicyclo[3.3.0]octo-2-ene (16) as a colorless oily product. Yield: 0.196 g (43%)

$^1$H NMR(CDCl$_3$)δ 0.73~1.06(3H,m), 1.04~2.90(23H,m), 2.90~4.17(3H,m), 3.63(3H,s), 4.33~4.71(1H,m), 5.10~5.66(2H,m), 5.94(0.67H,d,J=12 Hz), 6.22(0.33H,d,J=16.5 Hz), 6.57(1H,dd,J=15 Hz,J=6 Hz), 6.86~7.33(1H,m).

7-2 Synthesis of (1S,5S,6S,7R)-3-[4-carbomethoxy-1(EZ)-butenyl]-6-[4,4-difluoro-3(RS)hydroxy-(E)-1-octenyl]-7-tetrahydropyranyloxy-bicyclo[3.3.0]octo-2-ene (17):

(1S,5S,6S,7R)-3-[4-Carbomethoxy-1(EZ)-butenyl]-6-[4,4-difluoro-3-oxo-(E)-1-octenyl]-7-tetrahydropyranyloxybicyclo[3.3.0]octo-2-ene (16) (0.196 g) was dissolved in methanol, to which sodium borohydride (0.015 g) was added at 0° C., and stirred for 30 minutes. After a usual work-up (1S,5S,6S,7R)-3-[4-carbomethoxy-1(EZ)-butenyl]-6-[4,4-difluoro-3(RS)hydroxy-(E)-1-octenyl]-7-tetrahydropyranyloxybicyclo[3.3.0]octo-2-ene (17) was obtained as a colorless oily product. Yield: 0.184 g (93%)

$^1$H NMR(CDCl$_3$)δ 0.70~1.03(3H,m), 1.03~2.72(24H,m), 2.85~3.23(1H,m), 3.23~3.96(2H,m), 3.63(3H,s), 3.96~4.35(1H,m), 4.46~4.68(1H,m), 5.05~6.35(5H,m).

7-3 Synthesis of (1S,2S,3R,5S)-(E)-7-(4-carbomethoxybutylidene)-2-[4,4-difluoro-3(RS)-hydroxy-(E)-1-octenyl]-3-tetrahydropyranyloxybicyclo[3.3.0]octane (18):

(1S,5S,6S,7R)-3-[4-Carbomethoxy-1(EZ)-butenyl]-6-[4,4-difluoro-3(RS)hydroxy-(E)-1-octenyl]-7-tetrahydropyranyloxybicyclo[3.3.0]octo-2-ene (17) (0.184 g) was dissolved in acetone and put in an autoclave, into which tricarbonyl chromium/methyl benzoate complex (0.021 g) was added, and then degassed. The mixture in the autoclave was stirred under hydrogen pressure (70 kg/cm$^2$) at 120° C. for 15 hours. The reaction mixture was concentrated under reduced pressure, and the obtained crude product was purified on column chromatography (hexane/ethyl acetate=7/2–3/1) to give (1S,2S,3R,5S)-(E)-7-(4-carbomethoxybutylidene)-2-[4,4-difluoro-3(RS)-hydroxy-(E)-1-octenyl]-3-tetrahydropyranyloxybicyclo[3.3.0]octane (18) as a colorless oily product. Yield: 0.175 g (95%)

$^1$H NMR(CDCl$_3$)δ 0.75~1.05(3H,m), 1.05~2.63(28H,m), 3.23~4.00(3H,m), 3.62(3H,s), 4.00~4.40(1H,m), 4.48~4.66(1H,m), 5.03~5.32(1H,m), 5.33~6.05(2H,m).

7-4 Synthesis of (1S,2S,3R,5S)-(E)-7-(4-carboxybutylidene)-2-[4,4-difluoro-3(RS)-hydroxy-(E)-1-octenyl]-3-tetrahydropyranyloxybicyclo[3.3.0]octane (19):

(1S,2S,3R,5S)-(E)-7-(4-Carbomethoxybutylidene)-2-[4,4-difluoro-3(RS)-hydroxy-(E)-1-octenyl]-3-tetrahydropyranyloxybicyclo[3.3.0]octane (18) (0.175 g) was dissolved into methanol, to which 1N aqueous solution of sodium hydroxide was added, and the mixture was stirred until the mixture became completely clear. After a usual work-up a crude product, (1S,2S,3R,5S)-(E)-7-(4-carboxybutylidene)-2-[4,4-difluoro-3(RS)-hydroxy-(E)-1-octenyl]-3-tetrahydropyranyloxybicyclo[3.3.0]octane (19), was obtained. Yield: 0.172 g $^1$H NMR (CDCl$_3$)δ 0.70~1.03(3H,m), 1.03~2.73(27H,m), 3.22~4.39(4H,m), 4.40~4.72(1H,m), 4.98~5.35(1H,m), 5.35~6.03(2H,m), 3.22~6.13(2H,brs).

7-5 Synthesis of (1S,2S,3R,5S)-(E)-7-(4-carboxybutylidene)-2-[4,4-difluoro-3-oxo-(E)-1-octenyl]-3-tetrahydropyranyloxybicyclo[3.3.0]octane (20):

(1S,2S,3R,5S)-(E)-7-(4-Carboxybutylidene)-2-[4,4-difluoro-3(RS)-hydroxy-(E)-1-octenyl]-3-tetrahydropyranyloxybicyclo[3.3.0]octane (19) (0.172 g) was subjected to Collins oxidation at room temperature. The mixture was stirred for 30 minutes, sodium hydrogen sulfonate was added, and then filtered. The filtrate was concentrated. The obtained crude product was purified on column chromatography (hexane/ethyl acetate=20/1–10/1) using a silica gel (CC-4) to give (1S,2S,3R,5S)-(E)-7-(4-carboxybutylidene)-2-[4,4-difluoro-3-oxo-(E)-1-octenyl]-3-tetrahydropyranyloxy-bicyclo[3.3.0]octane (20). Yield: 0.050 g (30%)

$^1$H NMR(CDCl$_3$)δ 0.66~1.03(3H,m), 1.03~2.75(27H,m), 3.24~4.08(3H,m), 4.36~4.68(1H,m), 5.07~5.36(1H,m), 6.52(1H,dd,J=15 Hz, J=6 Hz), 6.83~7.30(1H,m), 7.20~8.20(1H,brs).

7-6 Synthesis of 16,16-difluoro-15-keto-9(O)-methano-PGI$_2$ (21):

(1S,2S,3R,5S)-(E)-7-(4-Carboxybutylidene)-2-[4,4-difluoro-3-oxo-(E)-1-octenyl]-3-tetrahydropyranyloxybicyclo[3.3.0]octane (20) (0.050 g) was dissolved in a mixture of acetic acid, water and THF (4:2:1), and stirred at 45° C. for 3.5 hours. The reaction mixture was concentrated under reduced pressure, and the obtained crude product was purified on column chromatography (hexane/ethyl acetate=4/1) using a silica gel (CC-4) to give 16,16-difluoro-15-keto-9(O)-methano-PGI$_2$ (21) as a colorless oily product. Yield: 0.033 g (80%)
$^1$H NMR(CDCl$_3$)δ 0.70~1.05(3H,m), 1.05~2.90(21H,m), 3.65~4.20(1H,m), 5.05~5.40(1H,m), 4.80~5.95(2H,brs), 6.53(1H,d,J=16 Hz), 7.07(1H,dd,J=16 Hz, J=7.5 Hz).
Synthetic Scheme I
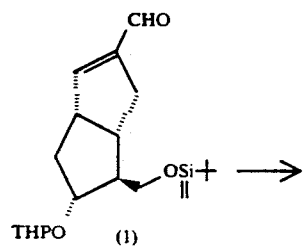
(1)
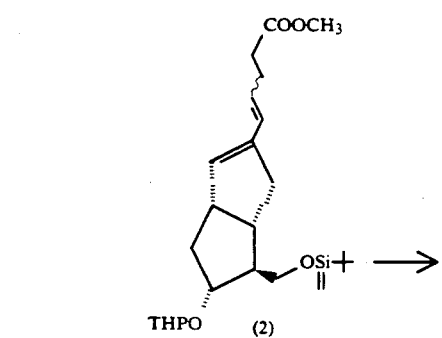
(2)
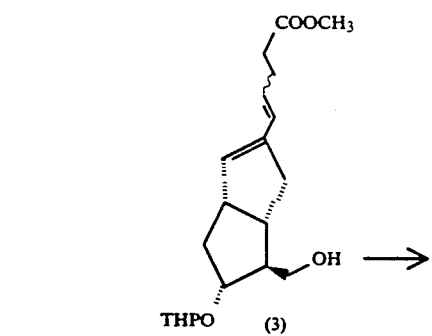
(3)
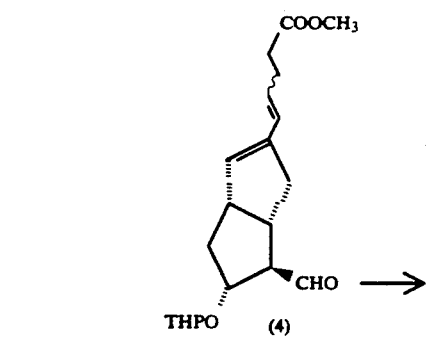
(4)
-continued
Synthetic Scheme I
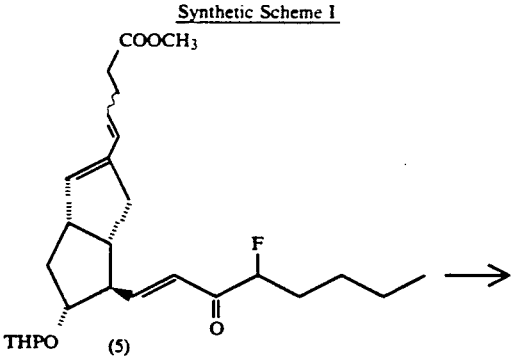
(5)
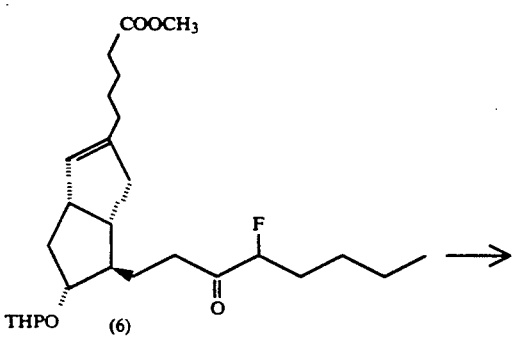
(6)
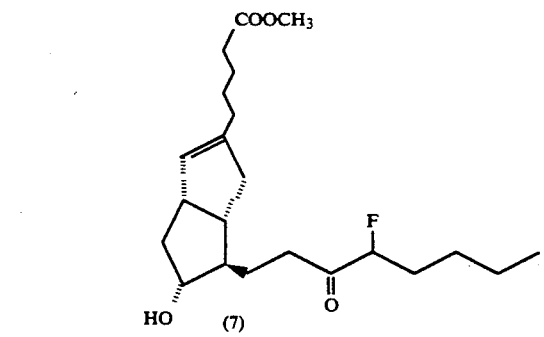
(7)
Synthetic Scheme II
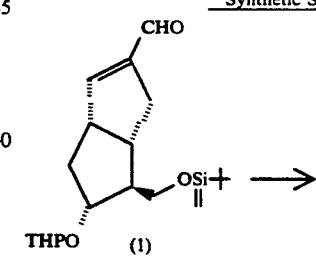
(1)
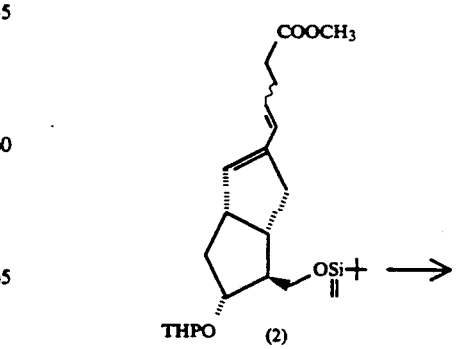
(2)

-continued
Synthetic Scheme II
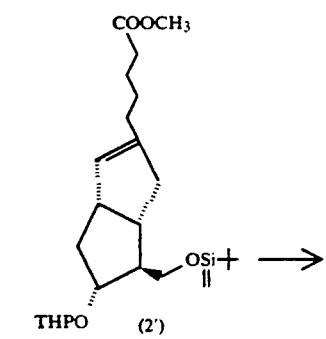
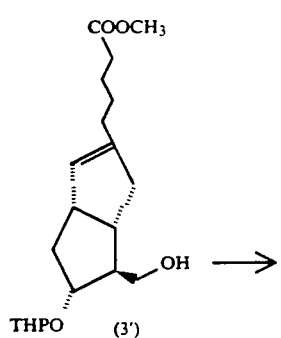
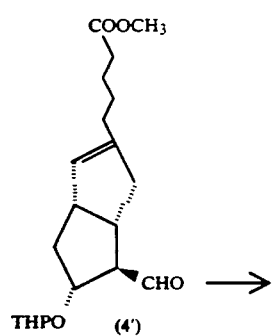
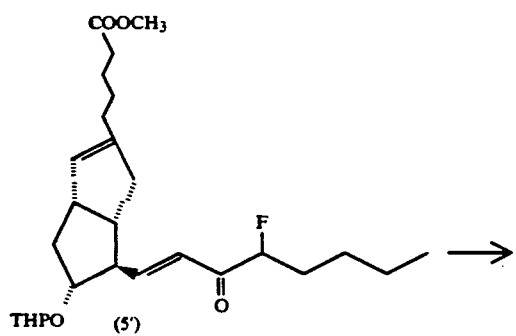
-continued
Synthetic Scheme II
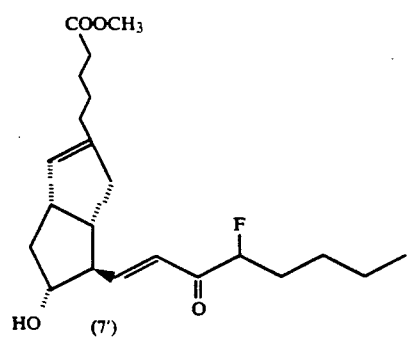
Synthetic Scheme III
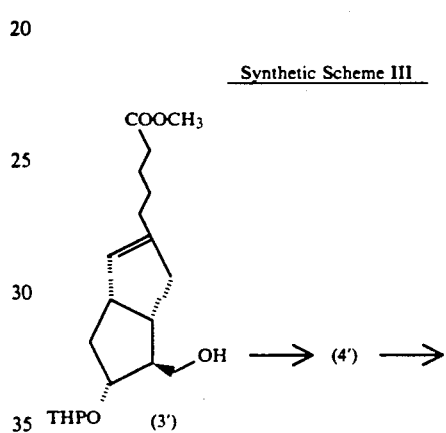
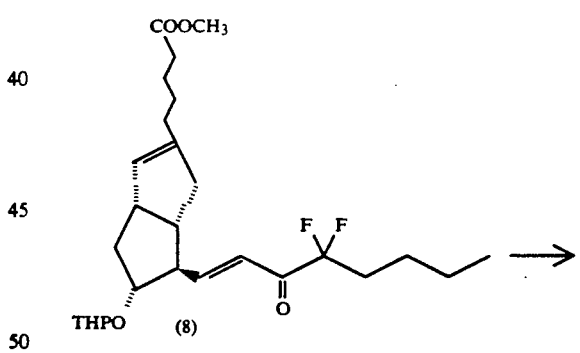
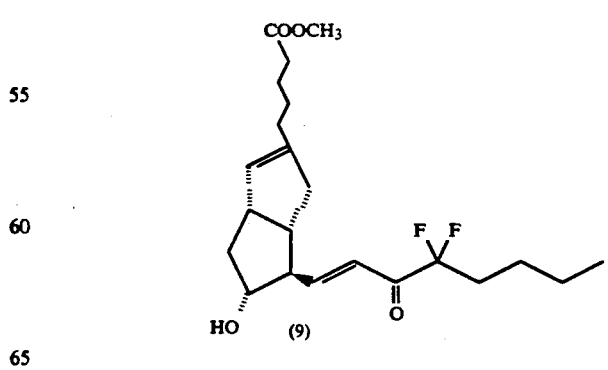

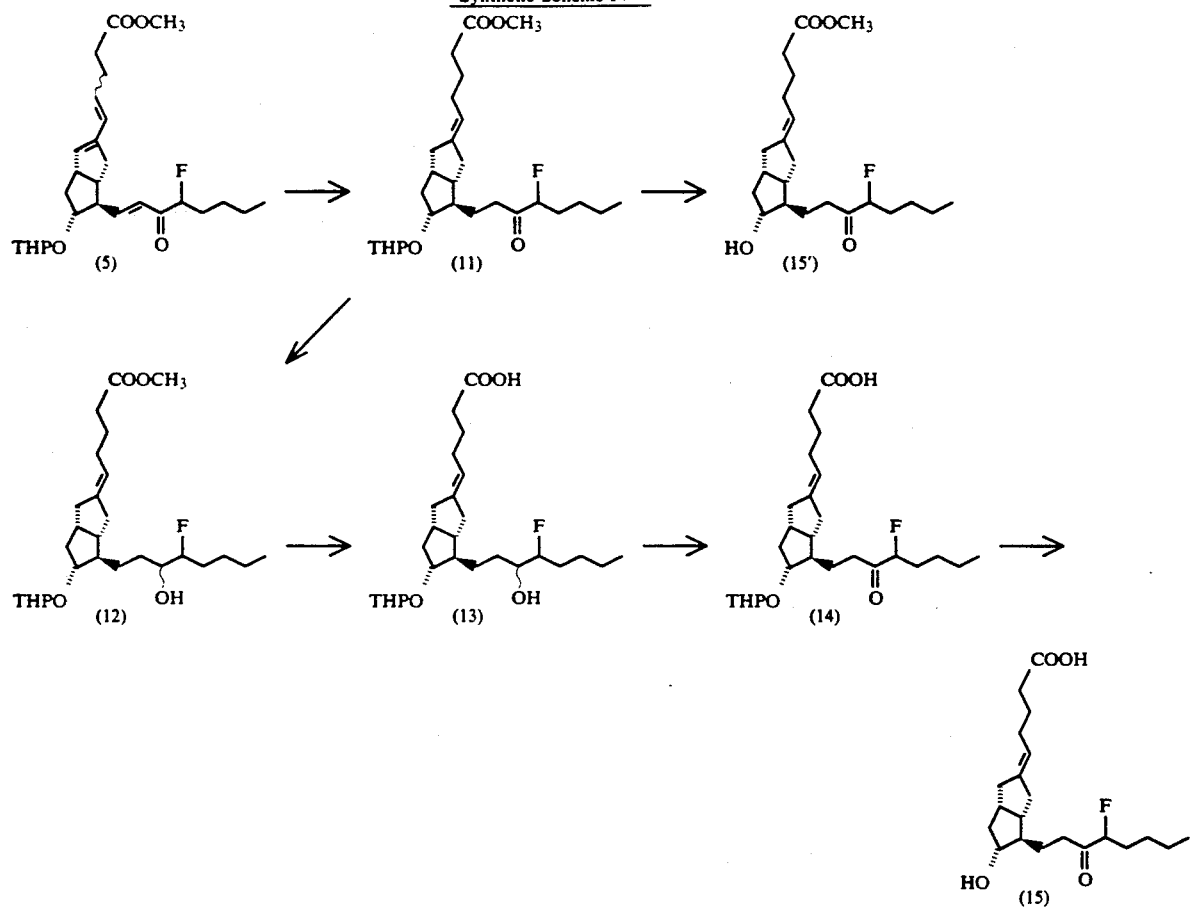
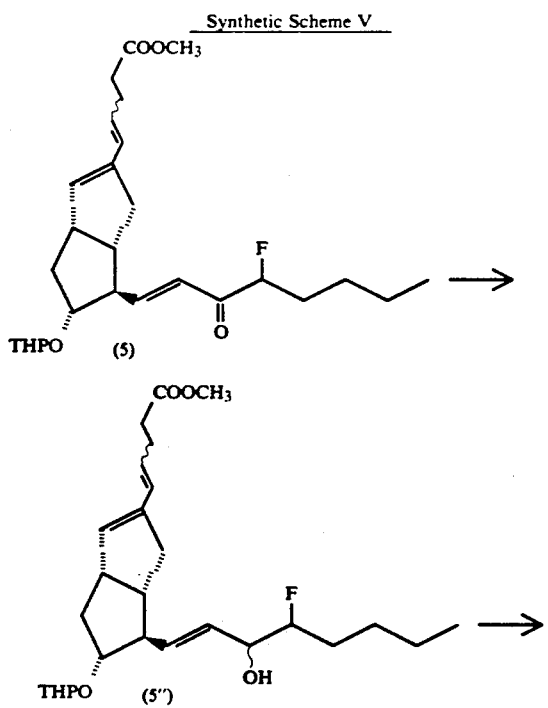

Synthetic Scheme V
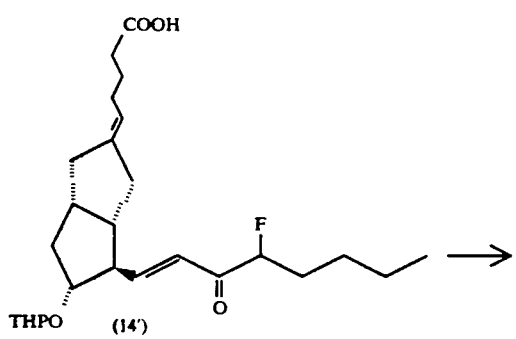
(14′)
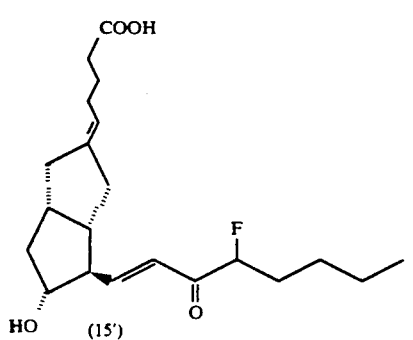
(15′)
Synthetic Scheme VI
(3) → (4) →
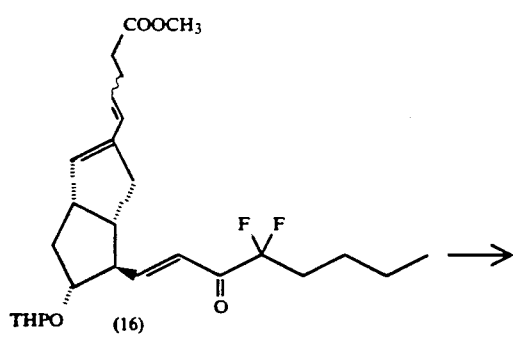
(16)
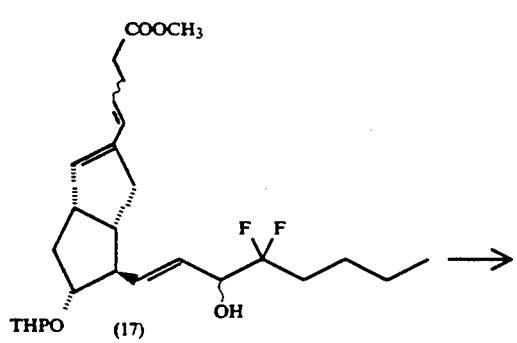
(17)
-continued
Synthetic Scheme VI
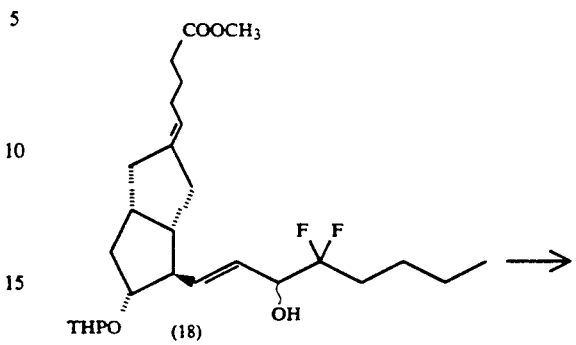
(18)
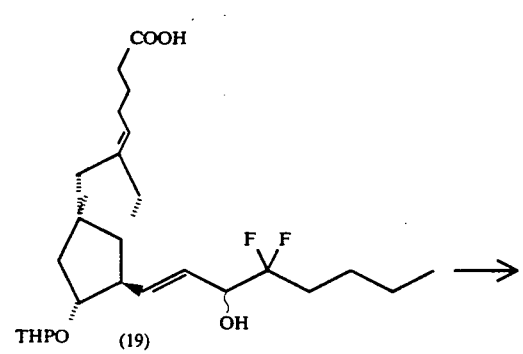
(19)
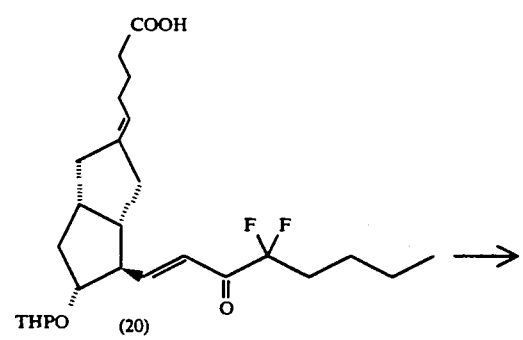
(20)
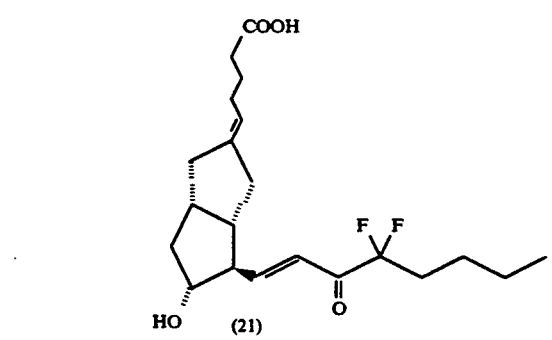
(21)
What is claimed is:
1. Prostaglandin Is represented by following formula (I) and (II);

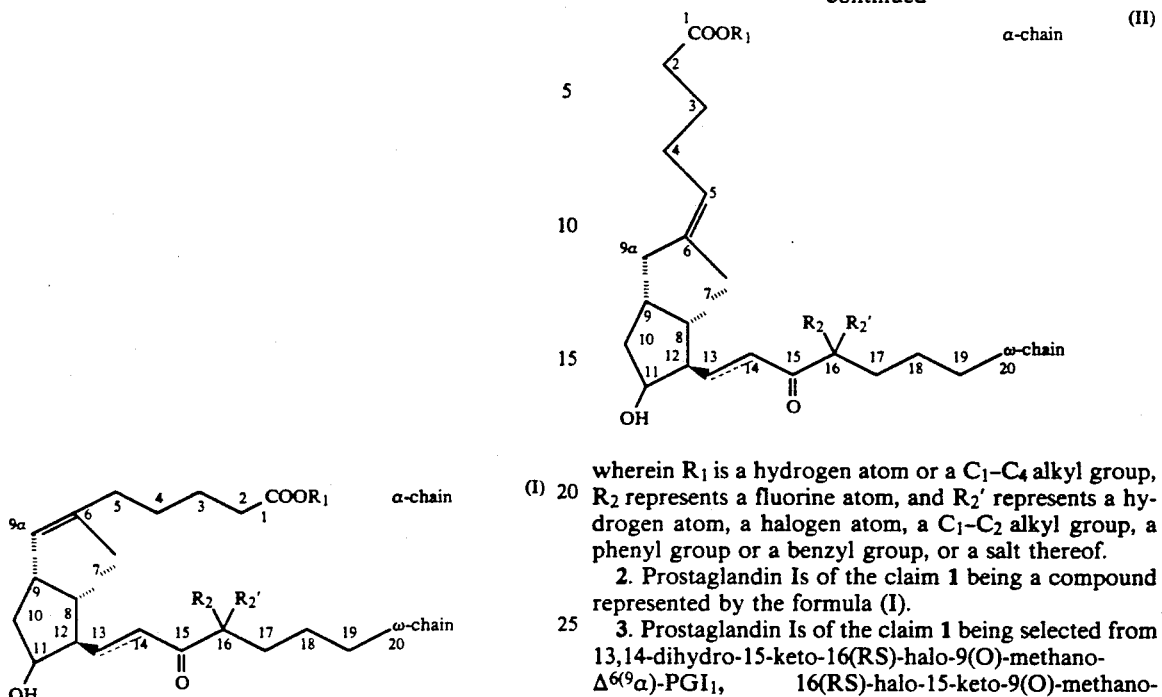

wherein $R_1$ is a hydrogen atom or a $C_1$–$C_4$ alkyl group, $R_2$ represents a fluorine atom, and $R_2'$ represents a hydrogen atom, a halogen atom, a $C_1$–$C_2$ alkyl group, a phenyl group or a benzyl group, or a salt thereof.

2. Prostaglandin Is of the claim 1 being a compound represented by the formula (I).

3. Prostaglandin Is of the claim 1 being selected from 13,14-dihydro-15-keto-16(RS)-halo-9(O)-methano-$\Delta^{6(9\alpha)}$-PGI$_1$, 16(RS)-halo-15-keto-9(O)-methano-$\Delta^{6(9\alpha)}$-PGI$_1$, 16,16-dihalo-15-keto-9(O)-methano-$\Delta^{6(9\alpha)}$-PGI$_1$, an alkyl ester, or a salt thereof.

4. Prostaglandin Is of the claim 1 being selected from 13,14-dihydro-15-keto-16,16-dihalo-9(O)-methano-PGI$_2$, 16(RS)-halo-15-keto-9(O)-methano-PGI$_2$, 16,16-dihalo-15-keto-9(O)-methano-PGI$_2$, an alkyl ester or a salt thereof.

5. Prostaglandin Is of claim 1, in which $R_2'$ is a fluorine atom.

* * * * *